US00PP15532P2

(12) United States Plant Patent
Yomo et al.

(10) Patent No.: US PP15,532 P2
(45) Date of Patent: Feb. 8, 2005

(54) ***ASARINA* PLANT NAMED 'SUN-ASARO'**

(50) Latin Name: ***Asarina lophospermum*×*Asarina erubescens***
Varietal Denomination: Sun-Asaro

(75) Inventors: Yasunori Yomo, Kawasaki (JP); Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/659,559

(22) Filed: Sep. 9, 2003

(51) Int. Cl.[7] ..... A01H 5/00
(52) U.S. Cl. ..... Plt./263
(58) Field of Search ..... Plt./263

(56) References Cited

PUBLICATIONS

The Seedsmen, 1990, 2 pages (including p. 17), published by Thompson & Morgan, published 1989 (characteristics of *Asarina erubescens*).

The Seed Catalogue 1999, 2 pages (including p. 27), published by Thompson & Morgan, published 1998 (characteristics and a photograph of *Asarina* "Red Dragon" which is a similar variety of "Sun–Asaro").

Application documents for Japanese PBR, Application No. 13722, proposed denomination: Sun–Asaware; Application Date: Aug. 10, 2001, Laid open date: Jan. 24, 2002 ("Sun–Asaware" is female parent of "Sun–Asaro").

W. Eilsens; Systematic Botany Monographs, vol. 5, The American Society of Plant Taxonomists, published May 9, 1985, pp. 68–71, 74–77 (Botanical explanation for species of *Lophospermum* sect.).

*Primary Examiner*—Kent Bell
(74) *Attorney, Agent, or Firm*—Christie, Parker and Hale, LLP

(57) ABSTRACT

Disclosed herein is an *Asarina* plant which has a creeping growth habit having short internode stem. The stem color is moderate yellow-green. The flower is a Penstemon-type and large. Both of the petal and the outside of corolla tube colors are strong purplish-red. The plant has a high resistance to heat, pests and diseases.

2 Drawing Sheets

Botanical/commercial classification: *Asarina lophospermum*×*Asarina erubescens*/*Asarina* Plant.
Varietal denomination: cv. 'Sun-Asaro'.

BACKGROUND OF THE VARIETY

The genus *Asarina* (*Lophospermum*), belonging to the *Scrophulariaceae,* plant is a herbaceous perennial, but is annual in a cold climate, and is frost hardy to frost tender. There are ten species in the genus *Asarina* (*Lophospermum*) and they are native from Mexico to Guatemala. The genus *Asarina* (*Lophospermum*) is similar to the genus *Antirrhinifnum,* but the differences are its flexible, scandent or clambering stems and its zygomorphic capsule. Corolla hues are various, such as red, violet, or dark purple distally, or whitish or light violet proximally. The *Asarina* plant grows in full light and in well-drained soil flowers in summer and the flowering period is long.

The *Asarina erubescens* (*Lophospermum erubescens*) plant is very vigorous plant, having long stems and internodes, and large flowers of which the edge is excurved. It has few flowers, because it grows very quickly and blooms only at the top of the stem. The *Asarina lophospermum* (*Lophospermum scandens*) plant has short stems and internodes, medium sized flowers of which the edge is incurved. Accordingly, this invention is aimed at obtaining a new variety having strong purplish-red colored, large excurved petals, together with a creeping growth habit, medium length internode, many branches, and a high resistance to heat, pests and diseases.

BREEDING PROCESS

First of all, self-pollination of 'Sun-Asaware' (non-patented in the United States), which was bred by crossing between *Asarina lophospermum* (*Lophospermum scandens*) as female parent and *Asarina erubescens* (*Lophospermum erubescens*) as male parent, was conducted in October 1998. In November, some seeds were obtained from the crossing. The seeds were sown and grown there in March 1999. In August 1999, 5 seedlings were selected in view of having the strong purplish-red, excurved and non-overlapped petal, and were propagated by cutting. Those seedlings were used in a trial by flower potting and bedding from May 2000. Finally one variety was selected in view of being no shorter than 'Sun-Asaware' (unpatented) and taller than 'Red Dragon' (unpatented). The botanical characteristics of that plant were then examined, using similar variety 'Red Dragon' for comparison. As a result, it was concluded that this *Asarina* plant is distinguishable from all other varieties, whose existence is known to us, and is uniform and stable in its characteristics. The new variety of *Asarina* plant was named 'Sun-Asaro'.

This *Asarina* plant 'Sun-Asaro' is presently maintained at 863-1, Aza-Iketani, Omori-cho, Yokaichi-shi, Shiga-ken, Japan.

This new and distinct variety of *Asarina* plant, 'Sun-Asaro', was asexually reproduced by tissue culture at the aforementioned and the homogeneity and stability thereof were confirmed. The new cultivar reproduces true to type in successive generations of asexual reproduction.

DESCRIPTION

In the following description, the color-coding is in accordance with The Horticultural Colour Chart of The Royal Horticultural Society, London, England (R.H.S. Colour Chart).

The botanical characteristics of the parent plant 'Sun-Asaware' (*Asarina lophospermum* (*Lophospermum scandens*)×*Asarina erubescens* (*Lophospermum erubescens*)) used in the breeding of 'Sun-Asaro' as follows.

Plant:
- *Growth habit*.—Creeping.
- *Height*.—Approximately 100 cm.

Stem:
- *Thickness*.—Approximately 2.9 mm.
- *Color*.—Strong yellow green (R.H.S. 143A).
- *Pubescence*.—Dense.
- *Branching*.—Many.
- *Internode length*.—Approximately 5.5 cm.

Leaf:
- *Arrangement*.—Alternate.
- *Shape*.—Triangular.
- *Margin*.—Dentate.
- *Length*.—Approximately 7.8 cm.
- *Width*.—Approximately 9 cm.
- *Color of upper side*.—Moderate olive-green (R.H.S. 146A).
- *Color of under side*.—Moderate yellow-green (R.H.S. 146B).
- *Thickness*.—Approximately 0.3 mm.
- *Length of petiole*.—Approximately 5.5 cm.
- *Attachment angle to stem*.—Upward.

Flower:
- *Shape*.—Normal-type.
- *Gap between upper-labiate petal and lower-labiate petal*.—Broad.
- *Diameter*.—Approximately 3.5 cm.
- *Width of corolla*.—Approximately 4.8 cm.
- *Length of tube*.—Approximately 7.2 cm.
- *Width of corolla tube*.—Approximately 2.2 cm.
- *Color of upper-labiate petal*.—Strong purplish-red (R.H.S. 70A).
- *Color of lower-labiate petal*.—Strong purplish-red (R.H.S. 70A).
- *Outside color of corolla tube*.—Strong purplish-red (R.H.S. 70A).
- *Type of upper-labiate petal*.—Medium.
- *Shape of lower-labiate petal*.—Overlapped.
- *Type of lower-labiate petal*.—Excurved.
- *Petal number*.—5.
- *Pubescence of corolla tube*.—Absent.
- *Shape of pistil*.—Hook-shaped.
- *Color of pistil*.—Light yellow-green (R.H.S. 2D).
- *Stamen number*.—4.
- *Color of anther*.—Light yellow-green (R.H.S. 145C).
- *Calix length*.—Approximately 3.2 cm.
- *Color of calyx*.—Brilliant yellow-green (R.H.S. 149A).
- *Peduncle length*.—Approximately 3.8 cm.
- *Peduncle thickness*.—Approximately 1.2 mm.
- *Color of peduncle*.—Vivid yellow-green (R.H.S. 144A).
- *Flowering time*.—Long.

Resistance:
- *Coldness*.—Medium.
- *Heat*.—Strong.
- *Diseases*.—Strong.
- *Pests*.—Strong.

The botanical characteristics of the similar variety *Asarina erubescens* (*Lophospermum erubescens*) used for examination as a comparison are as follows.

Plant:
- *Growth habit*.—Climber.
- *Height*.—More than 100 cm.

Stem:
- *Thickness*.—Approximately 3.5 mm.
- *Color*.—Moderate yellow-green (R.H.S. 146B).
- *Pubescence*.—Dense.
- *Branching*.—Many.
- *Internode length*.—Approximately 7.5 cm.

Leaf:
- *Arrangement*.—Arternate.
- *Shape*.—Triangular.
- *Margin*.—Crenate.
- *Length*.—Approximately 8 cm.
- *Width*.—Approximately 8.5 cm.
- *Color of upper side*.—Moderate olive-green (R.H.S. 146A).
- *Color of under side*.—Moderate yellow-green (R.H.S. 147B).
- *Thickness*.—Approximately 0.3 mm.
- *Length of petiole*.—Approximately 5.2 cm.
- *Attachment angle to stem*.—Upward.

Flower:
- *Shape*.—Normal-type.
- *Gap between upper-labiate petal and lower-labiate petal*.—Broad.
- *Diameter*.—Approximately 4.4 cm.
- *Width of corolla*.—Approximately 4.7 cm.
- *Length of tube*.—Approximately 7.5 cm.
- *Width of corolla tube*.—Approximately 3.6 cm.
- *Color of upper-labiate petal*.—Vivid purplish-red (R.H.S. 63B).
- *Color of lower-labiate petal*.—Vivid purplish-red (R.H.S. 63B).
- *Outside color of corolla tube*.—Moderate purplish-red (R.H.S. 64C).
- *Type of upper-labiate petal*.—Medium.
- *Shape of lower-labiate petal*.—Non-overlapped.
- *Type of lower-labiate petal*.—Excurved.
- *Petal number*.—5.
- *Pubescence of corolla tube*.—Present.
- *Shape of pistil*.—Hook-shaped.
- *Color of pistil*.—Light yellow-green (R.H.S. 2D).
- *Stamen number*.—4.
- *Color of anther*.—Light yellow-green (R.H.S. 145C).
- *Calyx length*.—Approximately 2.2 cm.
- *Color of calyx*.—Vivid yellow-green (R.H.S.144A).
- *Peduncle length*.—Approximately 4.8 cm.
- *Peduncle thickness*.—Approximately 1.5 mm.
- *Color of peduncle*.—Brilliant yellow-green (R.H.S. 149A).
- *Flowering period*.—Long.

Resistance:
- *Coldness*.—Medium.
- *Heat*.—Strong.
- *Diseases*.—Strong.
- *Pests*.—Strong.

The botanical characteristics of the similar variety 'Red Dragon' used for examination as a comparison are as follows.

Plant:
*Growth habit.*—Creeping.
*Height.*—Approximately 15 cm.
Stem:
*Thickness.*—Approximately 2.7 mm.
*Color.*—Moderate yellow-green (R.H.S. 137C).
*Pubescence.*—Normal.
*Branching.*—Many.
*Internode length.*—Approximately 2.8 cm.
Leaf:
*Arrangement.*—Alternate.
*Shape.*—Triangular.
*Margin.*—Dentate.
*Length.*—Approximately 6.8 cm.
*Width.*—Approximately 4.5 cm.
*Color of upper side.*—Grayish-olive-green (R.H.S. 147A).
*Color of under side.*—Moderate yellow-green (R.H.S. 147B).
*Thickness.*—Approximately 0.15 mm.
*Length of petiole.*—Approximately 4 cm.
*Attachment angle to stem.*—Upward.
Flower:
*Shape.*—Normal-type.
*Gap between upper-labiate petal and lower-labiate petal.*—Broad.
*Diameter.*—Approximately 1.8 cm.
*Width of corolla.*—Approximately 2.2 cm.
*Length of tube.*—Approximately 6.6 cm.
*Width of corolla tube.*—Approximately 1.7 cm.
*Color of upper-labiate petal.*—Moderate purplish-red (R.H.S. 58A).
*Color of lower-labiate petal.*—Moderate purplish-red (R.H.S. 58A).
*Outside color of corolla tube.*—Moderate purplish-red (R.H.S. 58A).
*Type of upper-labiate petal.*—Medium.
*Shape of lower-labiate petal.*—Overlapped.
*Type of lower-labiate petal.*—Incurved.
*Petal number.*—5.
*Pubescence of corolla tube.*—Absent.
*Shape of pistil.*—Hook-shaped.
*Color of pistil.*—Light yellow-green (R.H.S. 2D).
*Stamen number.*—4.
*Color of anther.*—Light yellow-green (R.H.S. 145C).
*Calyx length.*—Approximately 3.1 cm.
*Color of calyx.*—Brilliant yellow-green (R.H.S. 149A).
*Peduncle length.*—Approximately 4.2 cm.
*Peduncle thickness.*—Approximately 1.3 mm.
*Color of peduncle.*—Strong yellow-green (R.H.S. 144B).
*Flowering period.*—Long.
Resistance:
*Coldness.*—Medium.
*Heat.*—Strong.
*Diseases.*—Strong.
*Pests.*—Strong.

SUMMARY OF THE VARIETY

The new *Asarina* plant has a creeping growth habit and has short internode stems. The stem color is moderate yellow-green. The flower is a Penstemon-type and large. Both of the petal and the outside of corolla tube colors are strong purplish-red. The plant has a high resistance to heat, pests and diseases.

BRIEF DESCRIPTION OF THE DRAWING

FIG. 1 is a photograph giving a partial view of the new variety of *Asarina* plant 'Sun-Asaro' planted in a pot.

FIG. 2 is a photograph of flowers of the new variety of *Asarina* plant 'Sun-Asaro'.

DESCRIPTION OF THE VARIETY

The botanical characteristics of this new and distinct variety of *Asarina* plant 'Sun-Asaro' are as follows. The plants shown in the photographs and described below were about 5 months old at the time of description and were grown in 21 cm diameter containers at 863-1, Aza-Iketani, Omori-cho, Yokaichi-shi, Shiga-ken, Japan.

Plant:
*Growth habit.*—Creeping.
*Diameter.*—Varies with growth conditions. When grown in ground, plant diameter is about 140 cm.
Stem:
*Length.*—About 70 cm.
*Thickness.*—Approximately 3.2 mm.
*Color.*—Moderate yellow-green (R.H.S. 146D).
*Pubescence.*—Dense.
*Branching.*—Many.
*Internode length.*—Approximately 2.8 cm.
Leaf:
*Arrangement.*—Alternate.
*Shape.*—Triangular.
*Margin.*—Dentate.
*Length.*—Approximately 7.8 cm.
*Width.*—Approximately 9 cm.
*Color of upper side.*—Strong yellow-green (R.H.S. 144A).
*Color of under side.*—Moderate yellow-green (R.H.S. 143C).
*Apex.*—Acute.
*Base.*—Cordate.
*Thickness.*—Approximately 0.2 mm.
*Diameter of petiole.*—About 1.3 mm.
*Length of petiole.*—Approximately 3.5 cm.
*Color of petiole.*—Near 60B.
*Attachment angle to stem.*—Upward.
Flower:
*Shape.*—Penstemon-type.
*Gap between upper-labiate petal and lower-labiate petal.*—Broad.
*Diameter.*—Approximately 4.4 cm.
*Width of corolla.*—Approximately 4.7 cm.
*Length of tube.*—Approximately 5.3 cm.
*Width of corolla tube.*—Approximately 1.8 cm.
*Color of upper-labiate petal (upper and lower surfaces).*—Strong purplish-red (near R.H.S. 63A).
*Color of lower-labiate petal (upper and lower surfaces).*—Strong purplish-red (near R.H.S. 63A).
*Outside color of corolla tube.*—Strong purplish-red (near R.H.S. 63A).
*Shape of lower-labiate petal.*—Non-overlapped.
*Curvature of lower-labiate petal.*—Excurved.
*Petal number.*—5. The upper labiate petal is two lobed and the lobe width is about 1.95 cm, and the depth of the lobation is about 1.56 cm. The apex of the lobes is cuspidate and the margin is entire. The lower labiate petal is three lobed and the width of the side lobes is about 2.0 cm and that of the center lobe is about 1.69 cm. The depth of the lobation of the lower labiate petal is about 2.2 cm and the apex of all three lobes is mucronate and the margin is entire.

*Pubescence of corolla tube.*—Present.

*Shape of pistil.*—Hook-shaped.

*Number of pistils/flower.*—4.

*Color of pistil.*—Light yellow-green (R.H.S. 2D).

*Stamen number.*—4.

*Color of anther.*—Light yellow-green (R.H.S. 145C).

*Calyx length.*—Approximately 3.2 cm.

*Color of calyx.*—Brilliant yellow-green (R.H.S. 145B).

*Peduncle length.*—Approximately 3.1 cm.

*Peduncle thickness.*—Approximately 1.1 mm.

*Color of peduncle.*—Moderate yellow-green (R.H.S. 146C).

*Flowering period.*—Long; from May to October at 863-1, Aza-Iketani, Omori-cho-Yokaichi-shi, Shiga-ken, Japan.

*Lastingness of bloom on plant.*—3 to 4 days.

*Time to produce a flowering plant.*—About 90 days after cuttings in a greenhouse.

Resistance:

*Coldness.*—Medium.

*Heat.*—Strong.

*Diseases.*—Strong.

*Pests.*—Strong.

This new variety of *Asarina* plant 'Sun-Asaro' is most suitable for hanging baskets.

COMPARISON WITH SIMILAR VARIETY

The new variety of *Asarina* plant 'Sun-Asaro' is different from a parent variety, *Asarina* 'Sun-Asaware' in the following points, 1. The plant height of 'Sun-Asaro' is much lower than that of 'Sun-Asaware'.
2. The internode length of 'Sun-Asaro' is much shorter than that of 'Sun-Asaware'.
3. The flower shape of 'Sun-Asaro' is Penstemon-type, while that of 'Sun-Asaware' is normal-type.
4. The color of whole petal and corolla tube of 'Sun-Asaro' is strong purplish-red (R.H.S. 63A), while the whole petal and corolla tube color of 'Sun-Asaware' is strong purplish-red (R.H.S. 70A).
5. The lower-labiate petal shape of 'Sun-Asaro' is non-overlapped while that of 'Sun-Asaware' is overlapped.
6. The pubescence of corolla tube of 'Sun-Asaro' is present while that of 'Sun-Asaware' is absent.

The new variety of *Asarina* plant 'Sun-Asaro' is different from a similar variety, 'Red Dragon' in the following points, 1. The plant height of 'Sun-Asaro' is much higher than that of 'Red Dragon'.
2. The flower of 'Sun-Asaro' is larger than that of 'Red Dragon'.
3. The color of whole petal and corolla tube of 'Sun-Asaro' is strong purplish-red (R.H.S. 63A) while that of 'Red Dragon' is moderate purplish-red (R.H.S. 58A).
4. The lower-labiate petal type of 'Sun-Asaro' is excurved while that of 'Red Dragon' is incurved.

What is claimed is:

1. A new and distinct variety of *Asarina* plant named 'Sun-Asaro' substantially as herein illustrated and described.

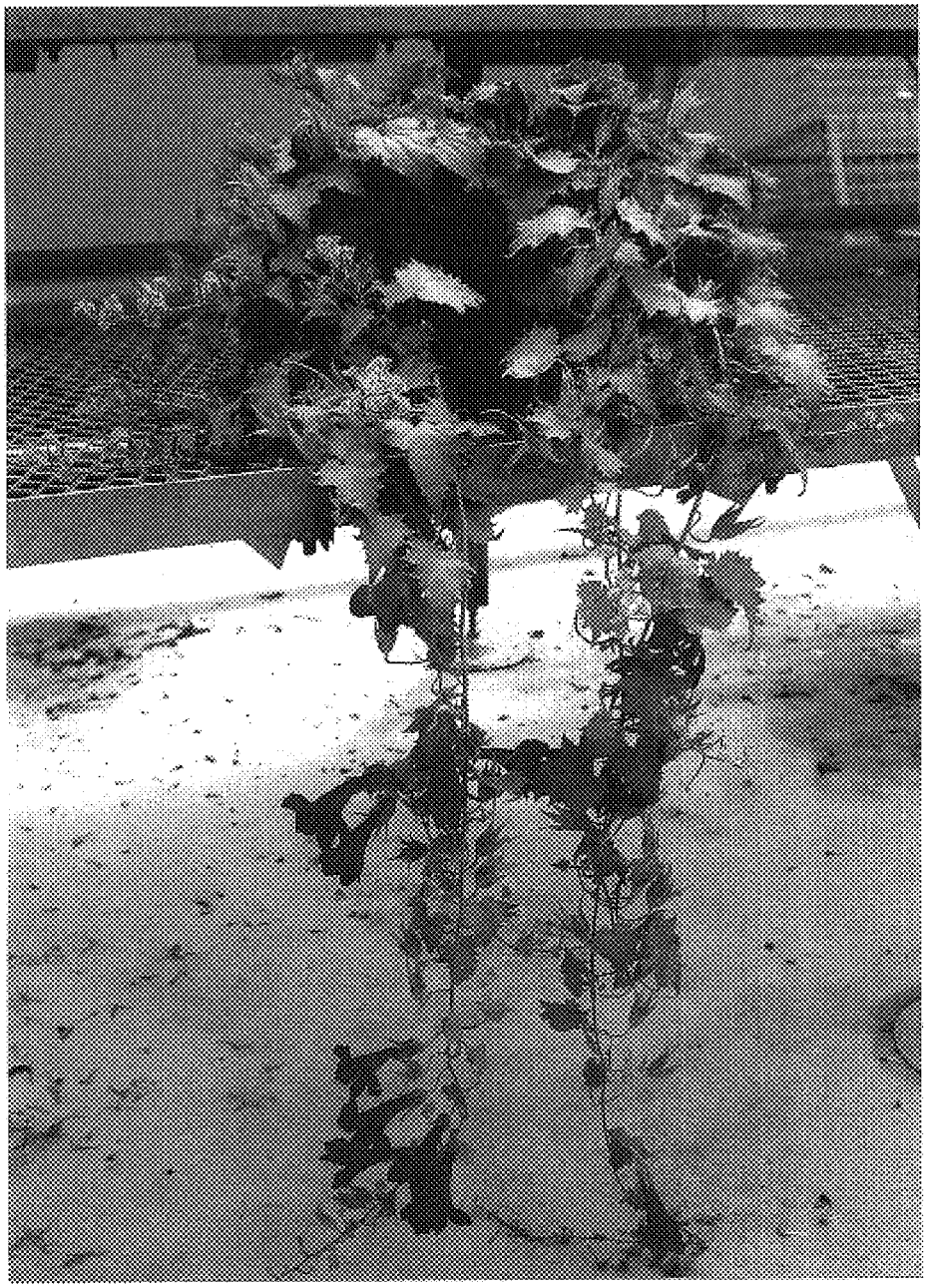

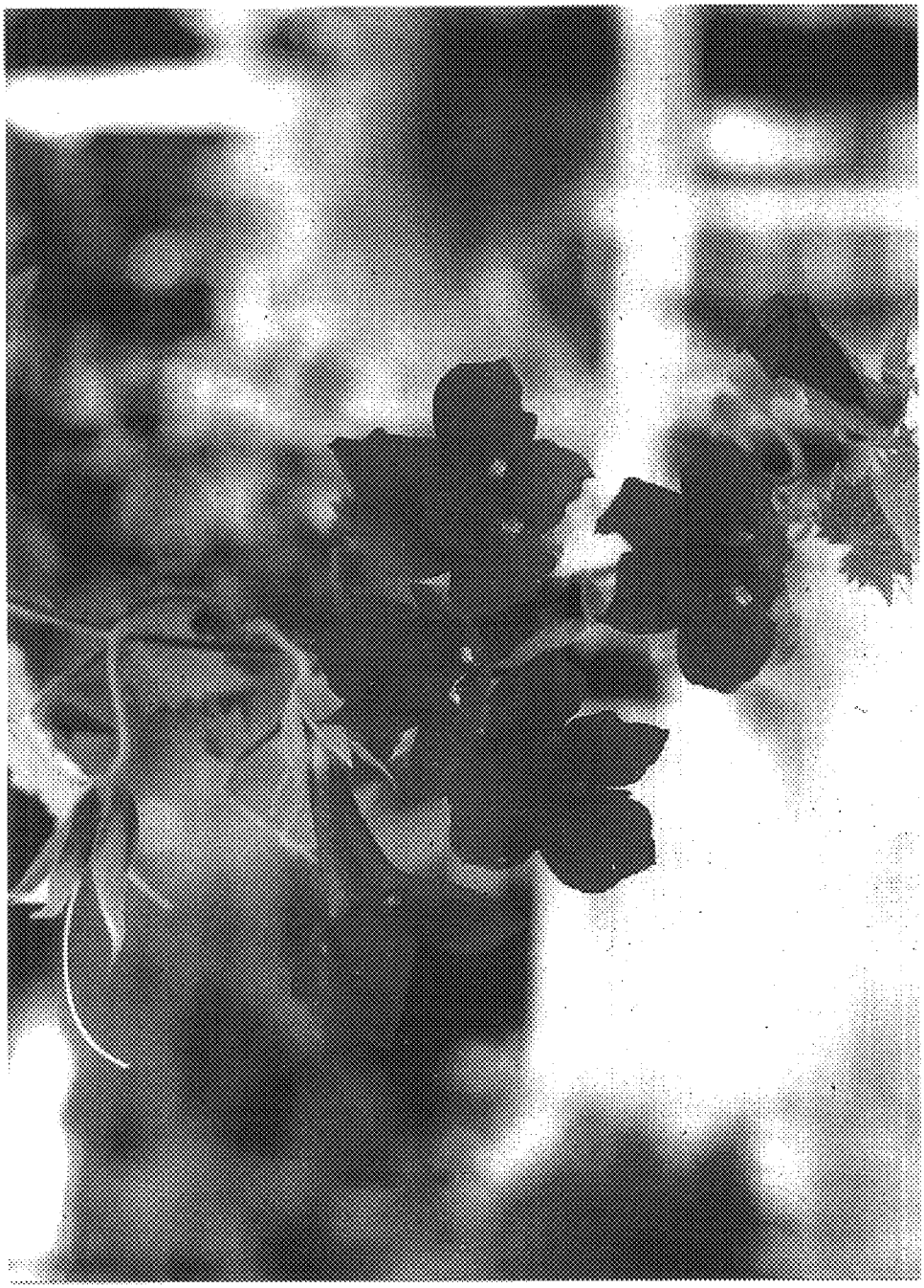

* * * * *